United States Patent
Garrigue

(10) Patent No.: US 10,485,910 B2
(45) Date of Patent: *Nov. 26, 2019

(54) REMOVABLE HEART PUMP, AND METHOD IMPLEMENTED IN SUCH A PUMP

(71) Applicant: FINEHEART, Pessac (FR)

(72) Inventor: Stephane Garrigue, Begles (FR)

(73) Assignee: FINEHEART, Pessac (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/641,535

(22) Filed: Jul. 5, 2017

(65) Prior Publication Data
US 2017/0296723 A1 Oct. 19, 2017

Related U.S. Application Data

(62) Division of application No. 14/235,200, filed as application No. PCT/FR2011/051830 on Jul. 28, 2011, now Pat. No. 9,731,057.

(51) Int. Cl.
*A61M 1/10* (2006.01)

(52) U.S. Cl.
CPC .......... *A61M 1/1031* (2014.02); *A61M 1/101* (2013.01)

(58) Field of Classification Search
CPC ...... A61M 1/11; A61M 1/122; A61M 1/1601; B25J 9/00
See application file for complete search history.

(56) References Cited

U.S. PATENT DOCUMENTS

| | | |
|---|---|---|
| 5,147,388 A | 9/1992 | Yamazaki |
| 5,507,629 A | 4/1996 | Jarvik |
| 5,888,241 A | 3/1999 | Jarvik |
| 6,135,729 A | 10/2000 | Aber |
| 6,217,541 B1 | 4/2001 | Yu |
| 6,234,772 B1 | 5/2001 | Wampler et al. |
| 6,406,422 B1 | 6/2002 | Landesberg |
| 7,022,100 B1 | 4/2006 | Aboul-Hosn et al. |
| 8,409,276 B2 | 4/2013 | Wampler |

(Continued)

FOREIGN PATENT DOCUMENTS

| | | |
|---|---|---|
| EP | 0764448 | 3/1997 |
| EP | 1129736 | 9/2001 |

(Continued)

OTHER PUBLICATIONS

International Search Report dated Jun. 6, 2012, corresponding to PCT/FR2011/051830 with English translation provided.

*Primary Examiner* — Bruce E Snow

(74) *Attorney, Agent, or Firm* — Young & Thompson

(57) ABSTRACT

The heart pump includes: a rotary impeller inserted in the systemic ventricle, the rotary impeller being provided with: a sealing membrane sutured onto the outer wall of the heart so as to secure the rotary impeller to the wall of the heart; a casing arranged inside the systemic ventricle such as to be able to suction and then discharge the blood; a preferably brushless motor connected to the casing and arranged inside the systemic ventricle and/or in the body of the ventricle, so as to facilitate maintenance; a managing unit installed in the epigastric region and including a preferably rechargeable power source and a unit for controlling the rotary impeller; a wired link between the managing unit and the rotary impeller; and a system for transmitting haemodynamic and rhythmic data measured by the heat pump via telemedicine.

16 Claims, 2 Drawing Sheets

(56) References Cited

U.S. PATENT DOCUMENTS

| | | |
|---|---|---|
| 2005/0107657 A1 | 5/2005 | Carrier et al. |
| 2006/0036127 A1 | 2/2006 | Delgado, III |
| 2008/0004485 A1 | 1/2008 | Moreschi |
| 2009/0024212 A1 | 1/2009 | Siess et al. |
| 2011/0144413 A1 | 6/2011 | Foster |
| 2011/0184224 A1 | 7/2011 | Garrigue |

FOREIGN PATENT DOCUMENTS

| | | |
|---|---|---|
| WO | 99/34847 | 7/1999 |
| WO | 00/44417 | 8/2000 |
| WO | 2004/101029 | 11/2004 |
| WO | 2010/010407 | 1/2010 |
| WO | 2011/092394 | 8/2011 |

REMOVABLE HEART PUMP, AND METHOD IMPLEMENTED IN SUCH A PUMP

The present invention relates to an artificial heart pump for regulating blood flow.

BACKGROUND OF THE INVENTION

The heart is a hollow muscle which by its rhythmic contraction ensures movement of the blood through the vessels. It comprises four chambers: the right atrium and the left atrium arranged in the upper part of the heart; the right ventricle and the left ventricle arranged in the lower part.

The right ventricle is intended to receive the blood coming from the right atrium and then eject it into the pulmonary artery. This constitutes the "pulmonary circulation" for sending the blood to the lungs to be reoxygenated.

The left ventricle receives the oxygenated blood from the lungs via the left atrium and then ejects it into the aorta for carrying oxygen to all the tissues of the body. This is the "major circulation", known as the systemic circulation.

Cardiac insufficiency (CI), a progressive inability of the heart to supply a sufficient blood flow to meet an individual's metabolic needs in everyday life, is the second commonest cause of death in Western countries. Treatment of cardiac insufficiency, which consists of increasing the blood flow in a manner appropriate to the needs of the patient, is not very effective with existing techniques, and is extremely costly.

Document US2009/0024212 is known, describing a pump for treating cardiac insufficiency due to inactivity of the sigmoid valves of the heart. This pump is of an elongated shape extending from the interior of the left ventricle to the interior of the aorta so as to replace the function of the valves.

Document U.S. Pat. No. 6,217,541 is also known, describing a heart pump which is also inserted through the aorta and into the ventricle. The end of the pump aspirates the blood contained in the left ventricle and then transfers it to the aorta via a flexible tube integral with the end of the pump and arranged through the valves.

The pumps described above require extremely complex fitting, and are not intended for permanent use.

Document U.S. Pat. No. 6,234,772 is also known, describing an implantable rotary pump. This pump is of the magnetic drive type and makes it possible to force the circulation of the blood while avoiding any stagnant area. This document says nothing regarding any effective fitting of the pump.

Document WO2010/010407 describes a cardiac assist rotary pump propelling blood from the left ventricle through the aortic valve. This pump is fixed through the aortic valve with fixing means in the aorta and at the ventricular apex. The electric motor is located in the conduit passing through the aortic valve.

Finally, document US2005/0107657 is known, describing a left ventricular assist pump (mixed-flow blood pump) with a so-called "radial" circuit for admission of the blood and a so-called "axial" circuit for ejection of the blood by means of a rotary propelling unit located at the centre of the device. The base is held within the left ventricular cavity by a semi-rigid rod through the apex of the ventricle, whereas the top of the device passes through the aortic valve with modification or functional suppression of this valve. Surgically, sternotomy with establishment of extracorporeal circulation is necessary, as an incision must be made at the root of the aorta. This document further discloses an equation of optimum efficiency between the diameter of the pump and the number of revolutions per minute of the propelling unit (up to 11,000 rpm). The diameter of the pump is given as ~20-22 mm.

SUMMARY OF THE INVENTION

A purpose of the present invention is a novel heart pump that is not complex to fit, compared to the putting in place of existing systems.

Another purpose of the invention is simple maintenance of said pump, which is intended for long-term use.

Yet another purpose of the invention is a pump that is not very invasive in the ventricle of the heart and is securely held in place.

At least one of the aforementioned purposes is achieved with a heart pump comprising:
   an impeller inserted in the systemic ventricle of a heart, through the wall of said heart, this impeller being provided with:
   a sealing and fixing membrane which is partly sutured to the external wall of the heart so as to make the impeller integral with the wall of the heart,
   a housing that is directly or indirectly integral with the sealing and fixing membrane, said housing being arranged within the systemic ventricle,
   a motor arranged in the systemic ventricle and/or in the thickness of the ventricle, for aspirating and then expelling the blood, from the bottom, into the systemic ventricle, outside the impeller and in the direction of sigmoid valves of the systemic ventricle, through the housing,
   a management unit comprising a power supply and a unit controlling the impeller; and
   a connecting wire between the management unit and the impeller.

In particular, the motor can be what is known as a "brushless" motor.

By systemic ventricle is meant the ventricle dedicated to the blood circulation for supplying a patient's body with oxygen via the aorta. In principle, this role is performed by the left ventricle, but in certain pathological situations this role can be performed by the right ventricle.

With the heart pump according to the invention, the impeller is securely fixed to the wall of the heart, and the patient can move about actively without risk of injury. The blood flow is acted upon directly, by directly controlling the blood circulation. The present pump is suitable for all patients with cardiac insufficiency without any prerequisites.

In the prior art, as described in documents US2005/0107657 and WO2010/010407 in particular, blood is directly propelled into the aorta as the pump passes through the aortic valve; this is not the case with the pump of the present invention. In the prior art, replacement of the pump requires very serious surgery as it involves the aortic valve.

The impeller can advantageously constitute a removable unit that is interchangeable via the wall of the systemic ventricle. Moreover, the arrangement and the form of the impeller in the systemic ventricle mean that this impeller is completely accessible from outside the ventricle, and therefore interchangeable, which allows simplified maintenance without serious surgical intervention of the sternotomy type. Replacement is easy in case of failure or wear.

Advantageously, the sealing and fixing membrane is fixed so as to ensure perfect sealing and make the impeller integral with the lower part of the heart near the cardiac apex.

The impeller according to the invention is a biocompatible impeller of various types, for example of the rotary or projection type.

Preferably, in the first case, the motor is of the rotary type and comprises a drive shaft of the rotor type equipped with vanes or with an endless screw, said drive shaft being arranged in the housing.

Preferably, the housing is a slender cylinder the side wall of which is of openwork construction so as to allow the flow of aspirated blood, and the axis of revolution of which is in the direction of the corresponding sigmoid valves. Such an arrangement allows ejection of the blood towards sigmoid valves, but also allows effective aspiration of the blood coming from the systemic atrium. By systemic atrium is meant the atrium associated with the systemic ventricle.

According to the invention, the management unit can be arranged outside the patient, but it is preferably internal, and advantageously in the epigastric region, in the upper part of the abdomen. Thus, in contrast to systems of the prior art, the power supply according to the invention is preferably implanted in its entirety, without externalization. For this purpose, the power supply can comprise at least one battery, and preferably a rechargeable battery; recharging of the battery can optionally be carried out by percutaneous transduction.

The pump according to the invention can thus be fully implanted and autonomous.

According to an advantageous feature of the invention, the pump can further comprise a sensor, a so-called activity sensor, for collecting data on cardiac activity so as to synchronize the operation of the impeller with the electrosystolic cardiac activity; this activity sensor can be connected to a wall of the heart. It can be connected by wire to the management unit. This configuration makes it possible to synchronize the operation of the impeller with the cardiac rhythm.

In a fully integrated configuration, the activity sensor is connected to the management unit via said connecting wire. In this case, this connecting wire constitutes the only link between the management unit and the impeller.

According to an advantageous embodiment of the invention, the heart pump comprises a sensor for collecting data on cardiac activity and for stimulation, known as a systemic sensor, connected to the wall of the systemic ventricle and able to communicate with the management unit by wire or wirelessly, in particular by wireless telemetry. This sensor plays a dual role of collecting cardiac information and of cardiac stimulation for contraction of the muscle in response to an instruction originating from the management unit. A second sensor of the same type, known as a non-systemic sensor, can be provided, connected to the wall of the non-systemic ventricle and able to communicate with the management unit by wire or wirelessly, in particular by wireless telemetry. In this case, these two sensors can be controlled for performing biventricular stimulation. Being able to stimulate the heart makes it possible to associate a direct action of the impeller on the blood flow with an indirect action of cardiac contraction. The cardiac rhythm detected by various sensors makes it possible, moreover, to synchronize the operation of the impeller with cardiac activity. In other words, the impeller is synchronized with the ventricular systolic activity when it is possible to collect information on cardiac activity, or it can operate continuously.

Another sensor for collecting data on cardiac activity and for stimulation can also be envisaged, known as an atrium sensor, connected to the wall of the systemic atrium and able to communicate with the management unit so as to supplement the system for collecting data on cardiac activity and for stimulation. Communication can be by wire or wireless, in particular by wireless telemetry.

A sensor is autonomous in energy when it communicates wirelessly with the management unit.

In particular in addition to the above, the pump according to the invention can advantageously comprise a sensor for collecting data on cardiac activity, for stimulation and for defibrillation, known as a defibrillation sensor, connected to the wall of the heart and connected by wire to the management unit; the control unit being moreover configured as a defibrillator.

Alternatively, a management unit can be provided, connected wirelessly to a defibrillator. The latter can be a defibrillator, external (cutaneous) or not, in particular automatic, implantable and independent but communicating with the management unit by electromagnetic waves.

According to an advantageous embodiment of the invention, moreover a second impeller as described above is arranged on the non-systemic ventricle and is also connected to the management unit.

In the context of telemedicine, the management unit comprises a wireless transmitter-receiver for data transfer for monitoring by telecardiology. These data can be haemodynamic and/or rhythm data, measured by all the sensors of the pump.

According to another aspect of the invention, a method is proposed for regulating the blood flow in a heart by means of a heart pump as described above. According to the invention, the blood flow is regulated by controlling the speed and duration of operation of the pump on the basis of predetermined control laws or on the basis of a control instruction relating to cardiac activity. With the control instruction, the blood flow is controlled in real time.

Advantageously, the control instruction is obtained by collecting data on cardiac activity by means of a sensor connected to the wall of the heart and connected by wire to the management unit. The blood flow can also be regulated by stimulating the heart by means of at least one stimulation sensor connected to the wall of the heart and connected by wire to the management unit.

BRIEF DESCRIPTION OF THE DRAWINGS

Other advantages and characteristics of the invention will become apparent on examination of the detailed description of an embodiment which is in no way limitative, and the attached diagrams, in which.

DETAILED DESCRIPTION OF THE PREFERRED EMBODIMENTS

Although the invention is not limited to this, a heart pump will now be described, implanted in the left ventricle of a heart, which is in principle the systemic ventricle. However, the invention can be applied in the same way to a right ventricle when the latter is the systemic ventricle.

Figure 1:
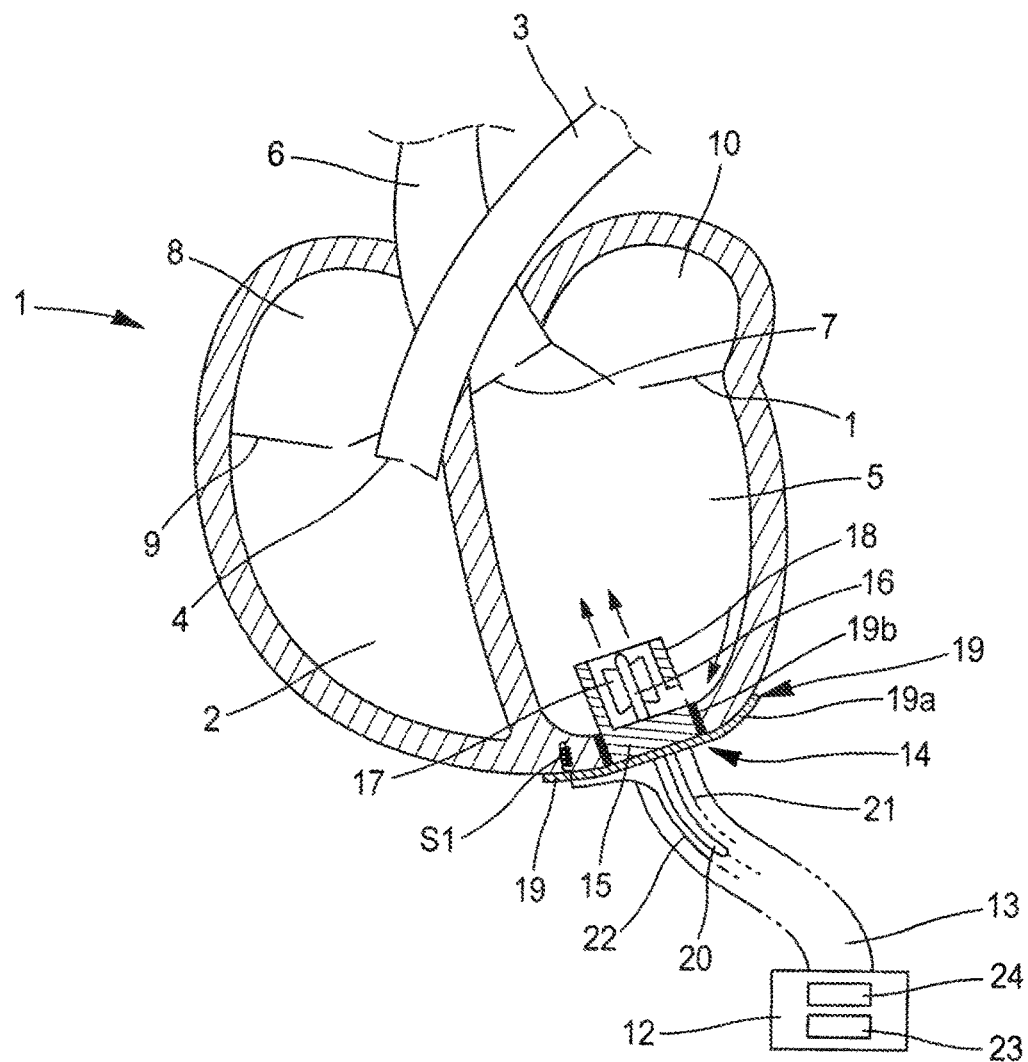
FIG. 1 is a simplified diagrammatic view of a heart pump according to the invention inserted in the left ventricle of a heart.
Figure 2:
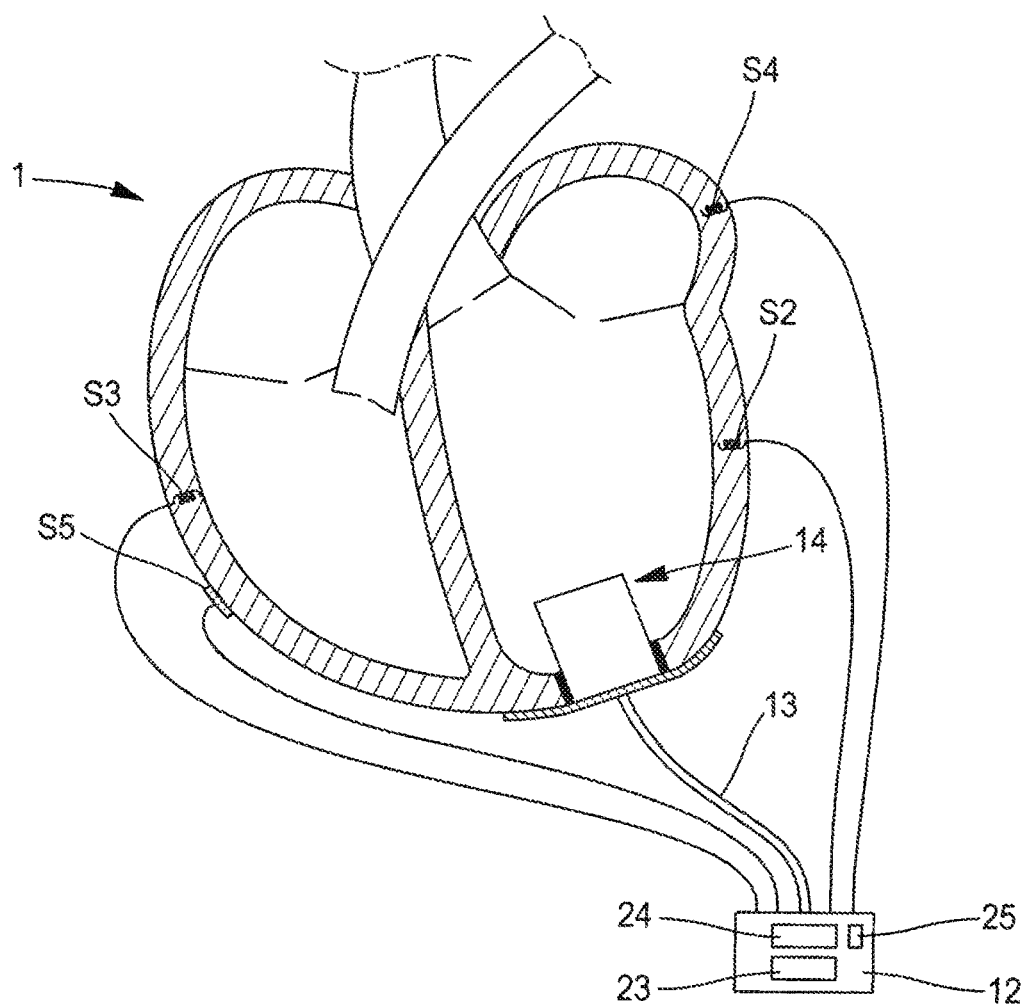
FIG. 2 is a diagrammatic view of a heart pump according to the invention equipped with a plurality of sensors or epicardial electrodes for effectively synchronizing the heart pump with the cardiac activity.

In FIGS. 1 and 2, the elements common to the different variants or embodiments bear the same reference numbers.

In FIGS. 1 and 2, the heart is denoted overall with the reference number 1. The right ventricle 2 can be seen, which has the function of ejecting the blood to the pulmonary artery 3 through the sigmoid valves 4. The left ventricle 5 has the function of generating the systemic circulation by ejecting the oxygen-rich blood to the aorta 6 via the sigmoid valves 7.

The right atrium 8 supplies the right ventricle 2 with blood via the atriopulmonary valves 9. The left atrium 10 supplies the left ventricle 5 with blood via the mitral valves 11.

The pump according to the invention comprises a management unit 12 connected by a connecting wire 13 to an impeller 14 inserted in the left ventricle 5, at the level of the apex, i.e. at the bottom pointed end of the left ventricle.

The impeller comprises a motor preferably of the brushless type 15 placed inside the left ventricle (or systemic ventricle) so that it is easily accessible following a minithoracotomy (surgical incision) and/or an operation by the epigastric route as opposed to a sternotomy where the chest is opened completely. This motor can be a motor with magnetic drive equipped with a rotor in the form of a drive shaft 16. The shaft can be of the "endless screw" type ("impeller") allowing ejection of blood from the bottom of the ventricle to the aorta 6. This shaft can also be a drive shaft with a propeller arranged on its free end. The conformation of this propeller is such that the blood fluid dynamics allows ejection of the blood to the aorta 6.

A housing 18 of cylindrical shape is provided, surrounding the drive shaft. This housing 18 comprises at least one opening, preferably several honeycomb openings for example, on its side wall so as to allow aspiration of blood coming from the left atrium and evacuation thereof via the top opening of the cylinder forming housing 18 by the action of the propeller, an endless screw or other means, 17. The rotation axis of the cylindrical housing 18 is directed towards the aortic orifice. Such an orientation is advantageously obtained when the impeller is put into place by suturing. A person skilled in the art will readily understand that other types of biocompatible miniaturized motors can be used for aspirating and ejecting the blood. In general, the materials used for implementing the pump according to the invention are biocompatible and can therefore be implanted in the patient's body.

The impeller 14 is inserted in the apex of the heart and is held there by means of a sealing and fixing membrane 19. Other types of membranes providing a perfect seal can be envisaged. This sealing and fixing membrane can comprise a sealing membrane 19a associated, i.e. connected directly or indirectly, with a fixing system 19b, such as a flange or any other system. The fixing system 19b is fixed to the motor and/or to the housing in the thickness of the heart wall. The sealing membrane 19a is preferably sutured on the external wall of the heart so as to ensure a perfect seal between the left ventricle 5 (or systemic ventricle) and the exterior of the heart.

The sealing and fixing membrane can be of varying shape with or without fixing system arranged in the thickness of the heart wall.

The connecting wire 13 connects the impeller 14 to the management unit 12, which comprises a power supply 23 such as a battery and a control unit 24, which can be configured remotely. The connecting wire 13 comprises a control line 21 enabling the control unit 24 to send control instructions to the impeller 14; the control line 21 can be bidirectional. Cable 20 is a cable for power supply of the motor of the impeller 15. Cable 22 allows the management unit 12 to be connected electrically to an optional activity sensor S1 inserted in the wall of the heart so as to collect data on the cardiac activity of the heart. The activity sensor S1 can be inserted through the sealing and fixing membrane 19 or else beyond it so as not to impair the hermeticity. It can, moreover, be capable of stimulating the left or the right ventricle. In these cases, it is arranged in the wall corresponding to the left ventricle or the right ventricle.

With such a heart pump according to the invention, the connection between the management unit 12 and the impeller 14 is provided by the single connection 13.

In operation, the control unit is configured so as to modulate the rotary speed and the duration of operation of the motor as a function of predetermined laws or control instructions. When a sensor is provided for collecting data on cardiac activity, for example the activity sensor S1, the control unit 24 can be configured for controlling the motor based on the cardiac rhythm, in real time. This form of control makes it possible to synchronize the rotary impeller with the heart rate.

Preferably, the management unit is implanted in the epigastric region, within the patient's abdomen. It is thus possible to provide for the control unit 24 to be configured remotely by wireless communication.

FIG. 2 shows an example of a heart pump according to the invention in an embodiment integrating a large number of sensors or epicardial electrodes.

The sensors arranged on the heart are of types for collection of data and for stimulation. They make it possible to identify the start of electrical activation and to synchronize the impeller with the opening of the valves. When the two ventricles are each subjected to an impeller, each impeller is synchronized with the opening of the corresponding valves. Advantageously, the frequency of each impeller is adjusted so as to preferably deliver a systolic ejection volume between 20 and 35 ml for each cardiac cycle.

Given that the actuation of an impeller in a ventricle with valve open (during systole) increases the quantity of blood ejected, the pump according to the invention makes it possible to increase the systolic ejection volume and consequently the blood flow.

According to the example illustrated in FIG. 2, the pump according to the invention comprises a sensor for collecting data on cardiac activity and for stimulation, known as a systemic sensor S2, in particular allowing the left ventricle to be stimulated by muscular contraction. This systemic sensor S2, connected to the management unit 12, is arranged in the wall of the heart at the level of the left ventricle. In the same way, another sensor for collecting data on cardiac activity and for stimulation, known as a non-systemic sensor S3, is arranged on the wall of the right ventricle and is connected to the management unit 12. In particular it allows stimulation of the right ventricle by muscular contraction. The combined action of the two sensors S2 and S3 allows biventricular stimulation to be carried out from the control unit 24 so as to maintain a cardiac rhythm according to a predetermined law or in response to instructions given.

FIG. 2 also shows, on the wall of the left atrium, a sensor for collecting data on cardiac activity and for stimulation, known as an atrium sensor S4, connected to the management unit 12. Advantageously, the control unit 24 can be configured for synchronizing the stimulation of the systemic S2 and non-systemic S3 sensors in relation to the information collected from this sensor S4.

In particular, in addition to the above, each of the sensors S2 and S4 can perform the role of the activity sensor S1.

In order to treat the risk of ventricular fibrillations, at least one epicardial patch or defibrillation sensor S5 is provided, arranged on the external wall of the heart, the control unit being configured both for detecting a situation of fibrillation and for delivering high-energy electric shocks.

For a full appreciation of cardiac activity, a patient activity sensor 25 is provided, such as an accelerometer or a pressure sensor, arranged for example in the management unit 12 or integrated with one of the aforementioned sensors. Such a sensor can be useful for a patient with chronotropic insufficiency, for detecting and informing the control unit of any acceleration of the patient's physical activity.

A haemodynamic sensor is also provided, for detecting the patient's haemodynamic state, in order to supplement the information obtained on cardiac rhythm and control the impeller efficiently. The haemodynamic sensor can be an endocardial acceleration sensor of the PEA (Peak Endocardial Acceleration) type, implanted for example together with the electrode S2.

The heart pump according to the invention therefore makes it possible to regulate the blood flow in order to prevent any cardiac insufficiency. Moreover, it can be implanted in the heart by mini-thoracotomy. The rotary impeller can be inserted at the apex (the pointed bottom end) of the left ventricle and if necessary a second rotary impeller can be inserted at the apex of the right ventricle. These two impellers can advantageously be connected to a management unit placed in the epigastric region. It is thus a closed system without externalization of electrical equipment and power supply.

Of course, the invention is not limited to the examples which have just been described and numerous adjustments can be made to these examples without exceeding the scope of the invention.

The invention claimed is:

1. A heart pump, comprising:
   a motor (15), sized to be located in a systemic ventricle of a heart, the motor (15) comprised of a housing (18) and a rotor (16) housed within the housing (18), the housing having a top opening, a sidewall containing at least one opening, and a bottom;
   a sealing and fixing membrane (19), configured to be attached to an external wall of the heart to hold the motor onto the heart in an implanted state with the housing extending through a thickness of a wall of the heart and into the ventricle,
   the sealing and fixing membrane (19) comprising a sealing membrane (19a), configured to be sutured to the external wall of the heart, and a fixing system (19b) configured to pass into the thickness of the wall of the heart and to attach to a portion of the side wall of the housing proximate to the bottom of the housing such that, in the implanted state when the heart pump is inserted into the systemic ventricle: (a) the fixing system (19b) is positioned inside the thickness of the wall of the heart and (b) the sealing membrane (19a) contacts the fixing system (19b) while being positioned outside the heart,
   the sealing membrane (19a) covering the bottom of the housing, and
   the housing of the motor being sized so that the top opening and the at least one opening of the sidewall are, in the implanted state, contained entirely within the ventricle,
   the motor configured to, in use in the implanted state, aspirate and then eject blood, from a bottom of the ventricle, into the at least one opening in the side wall of the housing, through the housing, and out of the top opening of the housing so as to flow into the ventricle and through sigmoid valves of the ventricle.

2. The heart pump according to claim 1, wherein the motor (15) is a brushless motor.

3. The heart pump according to claim 1, wherein the sealing and fixing membrane (19) is capable of being removably partly sutured so that the motor is removable through the wall of the heart.

4. The heart pump according to claim 1, wherein the sealing and fixing membrane (19) is capable of being fixedly partly sutured so as to ensure a seal with the heart and to make the heart pump integral with a lower part of the heart.

5. The heart pump according to claim 1,
   wherein the housing (18) is a cylinder,
   wherein the side wall of the housing is formed of openwork construction so as to allow the flow of aspirated blood, and
   wherein an axis of revolution of the motor extends in a direction of a sigmoid valve.

6. A method for regulating the blood flow in a heart by means of a heart pump system, comprising:
   controlling speed and duration of operation of a heart pump based on predetermined control laws or a control instruction relating to cardiac activity,
   wherein said heart pump system comprises a heart pump which comprises:
      a motor (15), sized to be located in a systemic ventricle of a heart, the motor (15) comprised of a housing (18) and a rotor (16) housed within the housing (18), the housing having a top opening, a sidewall containing at least one opening, and a bottom,
      a sealing and fixing membrane (19), configured to be attached to an external wall of the heart to hold the motor onto the heart in an implanted state with the housing extending through a thickness of a wall of the heart and into the ventricle,
      the sealing and fixing membrane (19) comprising a sealing membrane (19a), configured to be sutured to the external wall of the heart, and a fixing system (19b) configured to pass into the thickness of the wall of the heart and to attach to a portion of the side wall of the housing proximate to the bottom of the housing such that, in the implanted state when the heart pump is inserted into the systemic ventricle: (a) the fixing system (19b) is positioned inside the thickness of the wall of the heart and (b) the sealing membrane (19a) contacts the fixing system (19b) while being positioned outside the heart,
      the sealing (19a) covering the bottom the housing, and
      the housing of the motor being sized so that the top opening and the at least one opening of the sidewall are, in the implanted state, contained entirely within the ventricle,
      the motor configured to, in use in the implanted state, aspirate and then eject blood, from a bottom of the ventricle, into the at least one opening in the side wall of the housing, through the housing, and out of the top opening of the housing so as to flow into the ventricle and through sigmoid valves of the ventricle;
   a management unit (12) comprising a power supply (23) and a control unit (24) for controlling the heart pump; and
   a connecting wire (13) that connects the management unit and the heart pump.

7. The method according to claim 6, wherein the control instruction is generated by collecting data on cardiac activity by a sensor connected to the wall of the heart and connected by wire to the management unit.

8. The method according to claim 6, wherein the blood flow is regulated by stimulating the heart by at least one stimulation sensor connected to the wall of the heart and connected by wire to the management unit.

9. A heart pump system, comprising:
(i) a heart pump, with a motor (15), sized to be located in a systemic ventricle of a heart of a user, the motor (15) comprised of a housing (18) and a rotor (16) sized to be inserted in the systemic ventricle (5) of a heart, through the wall of said heart, the heart pump further including:
a sealing and fixing membrane (19), configured to be attached to an external wall of the heart to hold the motor onto the heart in an implanted state with the housing extending through a thickness of a wall of the heart and into the ventricle,
the sealing and fixing membrane (19) comprising a sealing membrane (19a), configured to be sutured to the external wall of the heart, and a fixing system (19b) configured to pass into the thickness of the wall of the heart and to attach to a portion of the side wall of the housing proximate to the bottom of the housing such that, in the implanted state when the heart pump is inserted into the systemic ventricle: (a) the fixing system (19b) is positioned inside the thickness of the wall of the heart and (b) the sealing membrane (19a) contacts the fixing system while being positioned outside the heart,
the sealing membrane (19a) covering the bottom of the housing, and
the housing of the motor being sized so that the top opening and the at least one opening of the sidewall are, in the implanted state, contained entirely within the ventricle,
the motor configured to, in use in the implanted state, aspirate and then eject blood, from a bottom of the ventricle, into the at least one opening in the side wall of the housing, through the housing, and out of the top opening of the housing so as to flow into the ventricle and through sigmoid valves of the ventricle;
(ii) a management unit (12), sized to be implanted in an abdomen of the user, and configured for removable connection with the heart pump outside the wall of the heart, the management unit comprising a power supply (23) and a control unit (24) for controlling the heart pump; and
(iii) a connecting wire (13) that provides said removable connection between the management unit and the heart pump outside the wall of the heart.

10. The system according to claim 9, wherein the management unit (12) is biocompatible so as to be arranged inside the user in an epigastric region.

11. The system according to claim 9, wherein the power supply (23) comprises at least one rechargeable battery.

12. The system according to claim 9, further comprising:
an activity sensor (S1) for collecting data on cardiac activity so as to synchronize the operation of the heart pump with electrosystolic cardiac activity, said activity sensor being configured for connection to a wall of the heart.

13. The system according to claim 9, further comprising:
a systemic sensor (S2) for collecting data on cardiac activity and for stimulation, said systemic sensor being configured for connection to the wall of the systemic ventricle and able to communicate with the management unit.

14. The system according to claim 9, wherein the management unit (12) is connected wirelessly to a defibrillator.

15. The system according to claim 9, further comprising:
a second heart pump sized to be located in a non-systemic ventricle of the heart, said second heart pump connected to said management unit.

16. The system according to claim 9, wherein the management unit (12) comprises a wireless transmitter-receiver for transmitting data for monitoring by telecardiology.

\* \* \* \* \*